United States Patent
Viravaux

(10) Patent No.: US 7,163,897 B2
(45) Date of Patent: Jan. 16, 2007

(54) METHOD FOR ASSAYING ELEMENTS IN A SUBSTRATE FOR OPTICS, ELECTRONICS, OR OPTOELECTRONICS

(75) Inventor: Laurent Viravaux, Le Fontanil (FR)

(73) Assignee: S.O.I.Tec Silicon on Insulator Technologies S.A., Bernin (FR)

( * ) Notice: Subject to any disclaimer, the term of this patent is extended or adjusted under 35 U.S.C. 154(b) by 141 days.

(21) Appl. No.: 10/637,073

(22) Filed: Aug. 6, 2003

(65) Prior Publication Data

US 2004/0029387 A1    Feb. 12, 2004

Related U.S. Application Data

(63) Continuation of application No. PCT/FR02/00521, filed on Feb. 12, 2002.

(30) Foreign Application Priority Data

Feb. 13, 2001    (FR) .................................. 01 01926

(51) Int. Cl.
*H01L 21/461*    (2006.01)
(52) U.S. Cl. ...................... 438/714; 438/714; 438/715; 438/716; 438/738; 216/96; 216/103; 216/104; 216/106; 356/36
(58) Field of Classification Search ............... 73/53.01; 438/14, 59; 216/2, 24, 59, 79, 83, 84, 93, 216/99
See application file for complete search history.

(56) References Cited

U.S. PATENT DOCUMENTS

| | | | |
|---|---|---|---|
| 3,273,963 A | 9/1966 | Gunn, Jr. ..................... 23/182 |
| 4,990,459 A | 2/1991 | Maeda et al. ................ 436/178 |
| 5,552,628 A | 9/1996 | Watanabe et al. ........... 257/632 |
| 5,849,597 A * | 12/1998 | Tokuoka et al. ............ 436/175 |
| 6,053,984 A | 4/2000 | Petvai et al. .................... 134/3 |
| 6,164,133 A * | 12/2000 | Watanabe ................... 73/432.1 |
| 2002/0101576 A1* | 8/2002 | Shabani et al. ................ 356/36 |

OTHER PUBLICATIONS

Callister, Materials Science and Engineering, 1997, 4th ed., John Wiley & Sons, pp. 605-607.*

* cited by examiner

*Primary Examiner*—Shamim Ahmed
*Assistant Examiner*—Maki Angadi
(74) *Attorney, Agent, or Firm*—Winston & Strawn LLP

(57) ABSTRACT

The invention provides a method of assaying at least one element in a material including silicon. The method includes the steps of decomposing a portion of the material with an etching agent to form a solution containing hexafluorosilicic acid and at least one element to be assayed, heating the solution to a temperature sufficient to transform a substantial portion of the hexafluorosilicic acid into silicon tetrafluoride and to cause at least some of the silicon tetrafluoride to evaporate, such that a solution for assaying is obtained in which the silicon content is reduced while and the elements to be assayed are conserved; and assaying at least one element contained in the solution. The invention is applicable to the field of manufacturing substrates or components for optics, electronics, or optoelectronics, and in particular to the field of quality control.

17 Claims, 1 Drawing Sheet

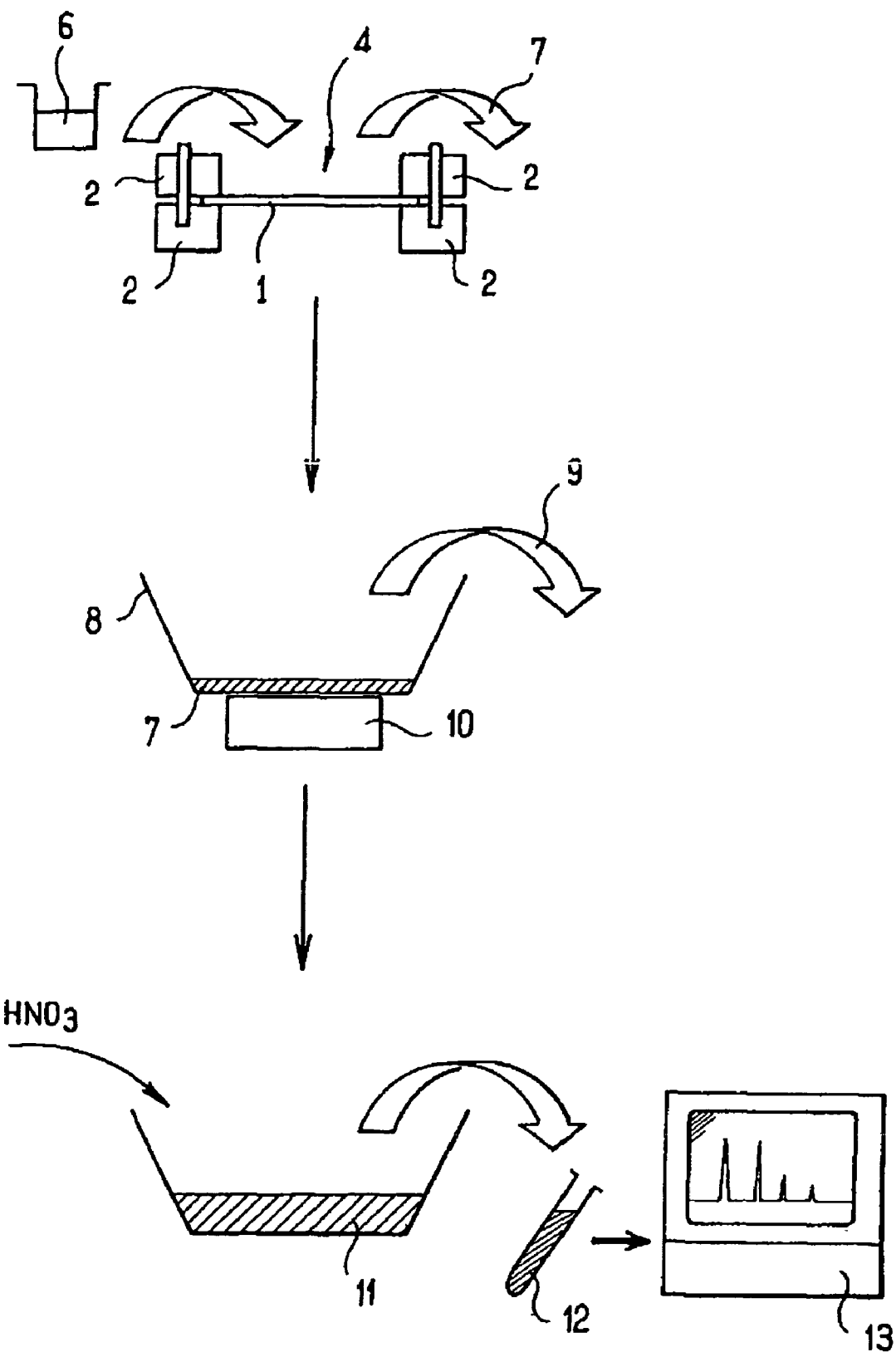

METHOD FOR ASSAYING ELEMENTS IN A SUBSTRATE FOR OPTICS, ELECTRONICS, OR OPTOELECTRONICS

CROSS-REFERENCE TO RELATED APPLICATION

The application is a continuation of International Application PCT/FR02/00521 filed Feb. 12, 2002, the entire content of which is expressly incorporated herein by reference thereto.

BACKGROUND

1. Field of the Invention

The invention relates to a method of assaying an element in a material comprising silicon, the material being intended in particular for manufacturing components for optics, electronics, or optoelectronics. For example, the invention can be used for assaying metal elements that might contaminate silicon substrates.

2. Background of the Invention

In silicon technology, the essential component in microelectronics is the metal-oxide-semiconductor (MOS) capacitor. The structure of a MOS capacitor comprises two electrodes (e.g., one made of metal or of polycrystalline silicon, and the other of monocrystalline silicon), separated by a fine insulating layer of silicon oxide ($SiO_2$) referred to as the "dielectric" or the "grid oxide". The grid oxide is made by thermal oxidation, with growth taking place on the surface and in depth. Thermal oxides are vitreous (or amorphous) materials that do not present long-distance crystallographic order, but merely chemical uniformity and short-distance order. Only 43% of the space in the crystal lattice is occupied, thus encouraging trapping and diffusion mechanisms. The presence of impurities gives rise to foreign species which occupy sites that are interstitial or substitutional. These impurities are mainly alkali ions (calcium, potassium, sodium) and metal ions (iron, aluminum, zinc, copper, nickel, . . . ).

If a substrate presenting such impurities in the active silicon layer is raised to high temperature, then the impurities can precipitate and thus lead to crystal defects forming.

Impurity diffusion gives rise to segregation of species and to localized high concentrations. These act as traps for charge carriers, providing energy levels that facilitate electron-hole recombinations. Such impurities degrade electrical performance, or can lead to dielectric breakdown in future circuits. Nowadays, the thickness of grid oxides can be as little as a few tens of angstroms (Å). For example, a layer which is 40 Å thick corresponds to about 20 layers of atoms. This small thickness exacerbates the impact of any defects. As a result, the quality of such a layer is intimately associated with the oxidation method and also with the quality of the substrate on which it is grown. In certain microelectronic applications, an oxide layer is formed beneath a semiconductor layer. Such an oxide layer is referred to as a "buried" oxide.

Buried oxides are used, for example, when making silicon on insulator (SOI) substrates. Substrates of that type can be used to make an electronic circuit on silicon insulated from a mechanical support by insulation, in this case the buried oxide. In a buried oxide, the presence of contaminants degrades electrical insulation between the circuit and the mechanical support. It is therefore important to assay such impurities.

Furthermore, numerous instruments made of a material comprising a high concentration of silicon, such as glass, quartz, etc., are used in methods of manufacturing substrates and components for microelectronics, optics, or optoelectronics. The performance of such substrates and such components depends in particular on the impurities they contain. Unfortunately, the instruments with which they are handled (such as quartz boats for substrates, for example) can contaminate them. Thus, in this case also, it can be desirable to assay the contaminants in such instruments.

Numerous techniques are already known for assaying elements, such as impurities, in a material.

Some of those techniques do not require the sample to be prepared. By way of example, those techniques comprise secondary ion mass spectrometry (SIMS) and total X-ray fluorescence (TXRF).

Other techniques require a sample to be prepared, for example merely by being put into solution. That applies in particular to atomic absorption spectrometry (AAS) and sometimes also to TXRF.

When samples are being prepared for an assay, it is necessary to avoid adding contaminants (operational contamination) or removing contaminants (precipitation, adsorption, etc.).

Known techniques of preparing samples for such assays consist in chemically etching the surface of a substrate.

One of those techniques is known to the person skilled in the art as vapor phase decomposition (VPD). Another of those techniques is known to the person skilled in the art as liquid phase decomposition (LPD).

The VPD techniques consists in etching the silicon oxide with hydrofluoric acid vapor. That reaction is generally performed at ambient temperature and it can be facilitated by cooling the material that is to be etched in order to encourage hydrofluoric acid vapor to condense on the material.

Etching occurs in accordance with the following reaction:

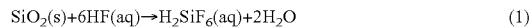
$$SiO_2(s) + 6HF(aq) \rightarrow H_2SiF_6(aq) + 2H_2O \quad (1)$$

That technique can also be used for decomposing native oxide, typically several tens of angstroms thick, on silicon or even thicker layers of oxide (e.g. several hundred angstroms thick) that have been deliberately formed, for example during thermal oxidation.

The LPD technique can be used both to etch silicon and to etch silicon oxide.

This technique can be used to etch oxides that are thick, typically several thousand angstroms thick to a few microns thick, or indeed a few tens of microns thick, e.g. as obtained by oxide deposition, with this being done by using a solution of hydrofluoric acid (HF).

Still using this technique, in order to etch silicon that has not been oxidized, for example, a mixture is used of nitric acid ($HNO_3$) and of hydrofluoric acid (HF). The reaction on silicon is then as follows:

$$Si + HNO_3 + 6HF \rightarrow H_2SiF_6 + NO_2 + H_2O + H_2$$

During such etching, several reactions take place simultaneously: the silicon is oxidized by the nitric acid and the silicon oxide is etched by the hydrofluoric acid.

In those two etching techniques, in vapor phase and in liquid phase, the various elements initially present in the silicon oxide or in the silicon are also passed into solution.

Assaying techniques other than AAS and/or TXRF cannot make do with those decomposition techniques only. This applies, for example, with inductively coupled plasma mass spectrometry (ICPMS), which has the particular advantage of being considerably faster than the above-cited techniques. The solution obtained after such preparatory steps, whether in liquid phase or in vapor phase, and when the thickness to be etched is large, has a silicon concentration that is typically equal to several grams per liter, which can represent a concentration that is too high for present-day ICPMS equipment (saturation of the analyzer, in particular concerning ionization of elements). The viscosity of the resulting solution is also incompatible with present-day ICPMS equipment. Under such circumstances, more advanced techniques are required for preparing the sample.

Thus, there is a need for improved assaying techniques to accurately determine impurities in such materials.

SUMMARY OF THE INVENTION

The present invention now provides an assaying technique that makes it possible to avoid the drawbacks of the methods described above while retaining good accuracy in assaying elements that are present at low concentration, or indeed to improve assaying accuracy.

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention is directed to a method of assaying at least one element in a material including silicon. The method includes the steps of decomposing a portion of the material with an etching agent to form a solution containing hexafluorosilicic acid and at least one element to be assayed, heating the solution to a temperature sufficient to transform a substantial portion of the hexafluorosilicic acid into silicon tetrafluoride and to cause at least some of the silicon tetrafluoride to evaporate, such that a solution for assaying is obtained in which the silicon content is reduced while and the elements to be assayed are conserved. The method also includes the step of assaying at least one element contained in the solution.

In further accordance with the invention, the decomposition step can include etching the material with the etching agent. The etching agent can be applied in the liquid phase or in a gaseous phase. Preferably, the etching agent can include a mixture of nitric acid and hydrofluoric acid.

In accordance with another aspect of the invention, the assaying step can include the use of inductively coupled plasma mass spectrometry. At least one element to be assayed is preferably chosen from the list consisting of sodium; calcium; potassium; aluminum; iron; copper; nickel; zinc; manganese; magnesium; chromium; cobalt; titanium; molybdenum; tungsten; boron; and phosphorous.

In accordance with another aspect of the invention, the temperature reached in the heating step can be less than the boiling point of hexafluorosilicic acid. Preferably, the temperature reached in the heating step is more than 70° C. but less than 100° C. Even more preferably, the temperature reached in the heating step is about 80° C.

In further accordance with the invention, the method can further include the steps of drying a volume of the solution for assaying and placing the dry residue back into solution. The drying step and placing steps are preferably performed after the heating step and before the assaying step. Additionally, the residue is preferably placed back into solution using a solution of nitric acid. Preferably, the dry residue is placed back into solution using a solution of hydrofluoric acid.

The solvent selected for putting the residue back into solution depends on the application intended by the operator, and is as a function, in particular, of the compounds and complexes that are to be made out of the element to be assayed, so that the compounds and complexes are soluble and stable once put back into solution. Thus, in order to assay iron, chromium, or sodium, the solvent used to put them back into solution is advantageously nitric acid, typically at a concentration of about 0.1%. To assay boron or phosphorous, it is advantageous to use hydrofluoric acid, typically at a concentration of about 1%. Other solvents can be more suitable for assaying other elements.

In accordance with another aspect of the invention, a substrate is provided that is made using the process described above. Preferably, an electronic component, optical component, opto-electronic component is provided made according to the process described above. Even more preferably, an electronic system wherein at least one of the components therein is made using the above-described process is provided.

In accordance with another aspect of the invention, the method uses the following reaction:

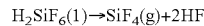

$$H_2SiF_6(l) \rightarrow SiF_4(g) + 2HF$$

In accordance with this aspect of the invention, the above-depicted reaction eliminates a large fraction of the silicon present in the solution produced during decomposition of the material comprising the silicon, so as to form a solution containing hexafluorosilicic acid.

The present assaying method can be used to detect impurities in silicon containing semiconductor materials so as to identify those materials that contain impurities that can reduce the properties or performance of the semiconductor material for use as a substrate in an intended application. Such intended applications include those where the semiconductor material substrate is made into a component for use in microelectronics, optics, or optoelectronics. As a result of the method, the semiconductor material substrate has a lower number of crystal defects and a lower number of localized high concentrations of impurities compared to semiconductor materials that have not been assayed.

Other aspects, objects and advantages of the invention will be better understood on reading the following detailed description of an implementation explained below.

BRIEF DESCRIPTION OF THE DRAWING

The invention will also be better understood on referring to the sole accompanying drawing FIGURE, wherein:

FIG. 1 is a diagram showing various operations in an implementation of the method of the invention.

DETAILED DESCRIPTION OF THE PREFERRED EMBODIMENTS

The invention is based on selective evaporation of the species present in the sample so as to eliminate silicon while retaining the elements that are to be assayed. This enables the concentration of silicon to be reduced to a level compatible with assaying techniques other than AAS. It is thus possible to use faster assaying techniques such as ICPMS. It has also been verified that the silicon depletion obtained by evaporating silicon tetrafluoride using the method of the invention can be performed without losing any significant quantity of the elements that are to be assayed. The assaying method of the invention thus remains very accurate, reliable, and very fast when combined with ICPMS. Furthermore, when combined with an AAS technique, for example, the method has the advantage of improving detection thresholds.

In further accordance with the invention, the decomposition reaction can be as follows:

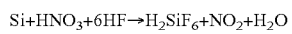

Si+HNO$_3$+6HF→H$_2$SiF$_6$+NO$_2$+H$_2$O

Reference will now be made in detail to the present preferred embodiments of the invention, examples of which are illustrated in the accompanying Figure. The implementation of the present invention corresponds to assaying contaminant elements in a silicon substrate.

For purpose of explanation and illustration, and not limitation, as shown in the figure, the substrate 1 is inserted between two pieces of Teflon® 2 to form a receptacle 4. The receptacle 4 is suitable for containing an etching solution 6. The etching solution 6 corresponds typically to a volume of 5 milliliters (ml) for a substrate 1 having a diameter of 125 millimeters (mm).

The etching solution 6 is preferably a mixture of nitric acid (HNO$_3$) and of hydrofluoric acid (HF). The concentration of nitric acid in the etching solution 6 is several tens of percent. The concentration of hydrofluoric acid in the etching solution 6 is several tens of percent.

After a certain thickness of the silicon of the substrate 1 has been dissolved, the resulting solution 7 obtained by liquid phase decomposition is poured into a receptacle 8 made of TEFLON® or any other equivalent material selected for its compatibility with the levels of contamination being assayed (polyethylene, PTFE, etc.).

Advantageously, etching is performed only to a depth of about 1 micron from the etched surface.

The receptacle 8 is then placed on a heater element 10, and its temperature is raised to a temperature lower than 100° C. so as to enable SiF$_4$ to be formed 9, and thus to evaporate off silicon, in accordance with the following reaction:

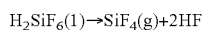

H$_2$SiF$_6$(l)→SiF$_4$(g)+2HF

It is important not to heat excessively so as to:

retain a temperature lower than the boiling temperature of the elements that are to be assayed or of the compounds or complexes that these elements form after decomposition and passing into solution; and avoid ejecting micro droplets, which would be harmful to the accuracy of the assay, particularly because of uncontrolled loss of some unknown quantity of the elements that are to be assayed.

Under normal pressure conditions, the boiling temperature of hydrofluoric acid is 112° C., so SiF$_4$ must be evaporated 9 at a temperature which is lower than this temperature of 112° C.

Advantageously, the evaporation temperature used lies in the range 70° C. to 100° C., and is preferably close to 80° C.

The elements that are typically desired to assay include sodium, calcium, potassium, aluminum, iron, copper, nickel, zinc, manganese, magnesium, chromium, cobalt, titanium, molybdenum, tungsten, boron, and phosphorous.

Under such conditions, it has been verified that the silicon can be evaporated off without losing the contaminants that are to be assayed.

The solution 7 obtained by liquid phase decomposition is thus evaporated until it becomes dry, and it is then put back into solution by adding 2 ml of 0.1% nitric acid to the dry residue in order to obtain a solution 11 for analysis.

With a volume of 5 ml of the solution obtained by liquid phase decomposition 7 put back into solution with 1 ml of nitric acid, the concentration of silicon in the solution for analysis 11 is less than one part per million (ppm). In addition, during the above-described implementation of the method of the invention, the contaminants for assaying are concentrated by a factor of 5 relative to the solution which would have been obtained using prior art techniques, i.e. in the selective evaporation step of the invention.

The 1 ml volume of solution for analysis 11 is then put into a test tube 12 for presentation to ICPMS analysis 13. ICPMS analysis is fast (analysis time typically 5 minutes) and accurate (detection thresholds of 100 parts per trillion (ppt)).

An implementation of the method of the invention is described above suitable for assaying contaminant elements in a silicon substrate. However, the method of the invention can be used in equivalent manner for assaying elements in SOI substrates, in surface oxidized silicon substrates, in quartz, in quartzware elements for heat treatment ovens, and the like.

It is also possible with the method of the invention to assay elements contained in VPD-etched silicon oxide.

The method of the invention can also be used for indirectly assaying elements in a material other than silicon. For example, to assay contaminants in an oven, it is possible to place a piece of material comprising silicon in the oven. The contaminants in the oven or in the other material placed in the vicinity migrate into the silicon and can then be assayed using the method of the present invention.

The method of the invention can be used not only for assaying contaminants, e.g., metal contaminants, but also for assaying dopants in a material, such as boron or phosphorous.

The resulting materials that are identified as having a low concentration of impurities are the preferred materials to be selected for us as substrates and components for microelectronics, optics, or optoelectronics. The performance of such substrates and such components is significantly improved due to the higher quality material that is selected. Thus, high quality materials that have a high concentration of silicon, such as glass, quartz, etc., are obtained for use in such instruments.

It will be apparent to those skilled in the art that various modifications and variations can be made in the present invention without departing from the spirit or scope of the invention. Thus, it is intended that the present invention include all such modifications and variations within the scope of the appended claims and their equivalents.

What is claimed is:

1. A method of assaying at least one element in an assay material that includes silicon, which method comprises:

decomposing a portion of the assay material by contacting that material with an etching agent in a liquid phase to directly form a first liquid solution containing hexa-fluoro-silicic acid and at least one element to be assayed;

heating the first liquid solution to a temperature of less 112° C. to transform a substantial portion of the hexa-fluoro-silicic acid in the first liquid solution into silicon tetrafluoride and to cause at least some of the silicon tetrafluoride to evaporate and form a resultant liquid solution for assaying in which the silicon content is reduced while conserving the at least one element to be assayed; and assaying at least one element contained in the solution.

2. The method of claim 1, wherein the etching agent includes a mixture of nitric acid and hydrofluoric acid.

3. The method of claim 1, wherein the assaying step includes the use of inductively coupled plasma mass spectrometry.

4. The method of claim 1, wherein at least one element to be assayed is chosen from the list consisting of sodium; calcium; potassium; aluminum; iron; copper; nickel; zinc; manganese; magnesium; chromium; cobalt; titanium; molybdenum; tungsten; boron; and phosphorous.

5. The method of claim 1 wherein the temperature reached the transforming step is more than 70° C. but less than 100° C.

6. The method of claim 1, wherein the temperature reached in the heating step is about 80° C.

7. The method of claim 1, further comprising the steps of drying a volume of the solution for assaying; and placing the dry residue back into solution.

8. The method of claim 7, wherein the drying step and placing steps are performed after the heating step and before the assaying step.

9. The method of claim 7, wherein the residue is placed back into solution using a solution of nitric acid.

10. The method of claim 7, wherein the dry residue is placed back into solution using a solution of hydrofluoric acid.

11. The method of claim 1, wherein the method is used to assay a dopant in a material.

12. The method of claim 11, wherein the dopant is chosen from the group consisting of boron and phosphorous.

13. The method of claim 1 wherein the material that includes silicon is a semiconductor material, and the assaying is used to detect impurities that reduce the properties or performance of the material when used as a substrate in an intended application.

14. The method of claim 13, wherein the intended application is one where the semiconductor material substrate is made into a component for use in microelectronics, optics, or optoelectronics.

15. The method of claim 14, wherein the semiconductor material substrate that is selected for the intended application is one that is assayed to have a lower number of crystal defects and a lower number of localized high concentrations of impurities compared to other substrates that are assayed.

16. The method of claim 1, wherein the resultant liquid solution is poured into a receptacle for further reduction and analysis.

17. A method for selecting a semiconductor material substrate for use in a microelectronic, optic, or optoelectronic application, which method comprises:

assaying, according to the method of claim 1, at least one impurity element in the semiconductor material substrate; and selecting for such application a substrate that has a lower level of that impurity element compared to other substrates so that the selected substrate will provide a lower number of crystal defects and a lower number of localized high concentrations of impurities.

* * * * *

UNITED STATES PATENT AND TRADEMARK OFFICE
CERTIFICATE OF CORRECTION

PATENT NO. : 7,163,897 B2 Page 1 of 1
APPLICATION NO. : 10/637073
DATED : January 16, 2007
INVENTOR(S) : Viravaux It is certified that error appears in the above-identified patent and that said Letters Patent is hereby corrected as shown below:

<u>Column 7</u>:
Line 19 (claim 6, line 2), after "reached in the", delete "heating" and insert
-- transforming --.
Line 24 (claim 8, line 2), after "placing steps are performed after the", delete "heating" and insert -- transforming --.

Signed and Sealed this

Sixth Day of March, 2007

JON W. DUDAS
*Director of the United States Patent and Trademark Office*